(12) United States Patent
Lorenzo

(10) Patent No.: US 6,439,958 B1
(45) Date of Patent: Aug. 27, 2002

(54) BREAST SAVER COMFORT

(76) Inventor: Aida Iris Lorenzo, 19 Broadway, Valley Stream, NY (US) 11580

( * ) Notice: Subject to any disclaimer, the term of this patent is extended or adjusted under 35 U.S.C. 154(b) by 0 days.

(21) Appl. No.: 09/690,631

(22) Filed: Oct. 17, 2000

Related U.S. Application Data

(60) Provisional application No. 60/160,230, filed on Oct. 18, 1999.

(51) Int. Cl.[7] .................................................. A41C 3/00
(52) U.S. Cl. ............................................ 450/1; 450/57
(58) Field of Search ............................... 450/1, 63, 79, 450/4, 57; 602/41, 75, 76, 79, 58, 60, 61, 19

(56) References Cited

U.S. PATENT DOCUMENTS

| | | | | |
|---|---|---|---|---|
| 1,592,496 A | * | 7/1926 | Madden | 602/19 |
| 3,189,028 A | * | 6/1965 | Domire | 450/1 |
| 3,968,803 A | * | 7/1976 | Hyman | 450/1 |
| 4,022,197 A | * | 5/1977 | Castiglia | 450/1 |
| 4,187,855 A | * | 2/1980 | Paulus et al. | 450/1 |
| 5,098,331 A | * | 3/1992 | Corrado | 450/58 |
| 5,137,508 A | * | 8/1992 | Engman | 602/79 |
| 5,152,741 A | * | 10/1992 | Farnio | 602/79 |
| 5,158,541 A | * | 10/1992 | McCurley | 602/79 |
| 5,429,593 A | * | 7/1995 | Matory | 602/79 |
| 5,527,270 A | * | 6/1996 | Chase et al. | 602/79 X |
| 5,538,502 A | * | 7/1996 | Johnstone | 602/79 |
| 5,843,018 A | * | 12/1998 | Shesol et al. | 602/79 |

* cited by examiner

*Primary Examiner*—Gloria M. Hale
(74) *Attorney, Agent, or Firm*—Ward & Olivo

(57) ABSTRACT

A chest band for use for comfort and breast stabilization from lateral gravitational breast shifting while the user lays in the right or left lateral position comprising a stretchable and adaptable body strip disposed to encircle the body, and first and second sections of the length of the body strip wherein the first section further comprises a semi-cylindrical component of a sponge-like material at one end and a nap material patch on its outer surface with a cylindrical side placed over the breast, between the breast and wherein the second section comprises a means for connecting an end of the body strip together in the form of a loop to encircle a user's body and wherein the chest band further comprises at least one fenestration[s] to enable[s] breast exposure.

The object of this invention is to provide a comfort band which is constructed from a combination of stretch woven materials with a semi-cylindrical shaped bolster centrally placed over the sternum and wrapped under the arms around the chest with a band and preferably secured with a hook and loop fastener type fastener thereby preventing lateral breast shifting when the patient is in the side-laying position. The stretchable band or garment of the invention comprises a relatively wide body strip which accommodates breast coverage or exposure achieved with a Fenestrated band.

2 Claims, 4 Drawing Sheets

BREAST SAVER COMFORT

This application claims priority from Provisional application Ser. No. 60/160,230, filed Oct. 18, 1999.

BACKGROUND OF THE INVENTION

This invention is directed to an underclothes garment, and more particularly to a garment used in the medical field to ease and prevent lateral gravitational breast shifting while the user is in the side-lying position.

In the past a traditional brassiere has been used to support the breast while in the upright position but does not provide adequate lateral support for the side-lying position. The brassier usually has metal or plastic parts which when used while sleeping or extended periods of bed rest produces pressure points and skin irritation. It is not worn as a "traditional" undergarment or serve the same function of strapped breast support while standing in an upright position.

BRIEF SUMMARY OF THE INVENTION

The object of this invention is to provide a comfort band which is constructed from a combination of stretch woven materials with a semi-cylindrical shaped bolster centrally placed over the sternum and wrapped under the arms around the chest with a band and preferably secured with a VELCRO™ (or similar hook and loop fastener) type fastener thereby preventing lateral breast shifting when the patient is in the side-laying position. The stretchable and adaptable band or garment of the invention comprises of a relatively wide body strip which accommodates breast coverage or exposure achieved with a Fenestrated band.

This invention is directed to the medical field as well as women's personal care. A more specific object of this invention is to provide a breast comfort band that will ease the discomfort of lateral breast shifting which occurs in the side lying position and caused by breast engorgement such as in mastitis, post partum engorgement, breast implants and anatomically heavy and large size of breast. In addition, it will absorb perspiration and prevent skin breakdown/deterioration caused by perspiration and prolonged direct skin contact such as seen in hospitalized geriatric patients. Immobile geriatric patients who favor the side lying position and have flaccid breast experience skin deterioration of the breast due to one breast resting on the other. This would be prevented with the breast saver comfort band in place, minimizing tissue injury/deterioration as well as reducing the incidence of nosocomial infections due to open skin ulcerations. This preventative practice will reduce medical care required such as use of antibiotic ointments or medicated gauzes to prevent any open skin from receiving pathogenic bacteria. The band may also be used to absorb serous or sanguineous drainage when used post-operatively with breast procedures such as in medial breast lumpectomy. The band's thickness measures only 2–4 mm's, it is not bulky or have metal or plastic parts thereby reducing the risk of creating new pressure points on fragile skin or dependent area. Unlike traditional brassieres the comfort band is used at night for lateral breast support.

In women's personal care the band will absorb uncomfortable perspiration from in between the breast while in the side lying position as well reduce or prevent medial breast wrinkling in mature women caused by extended periods of lateral breast shifting. This wrinkling preventative measure may be used in conjunction with topical cosmetic creams or lotions.

Other objects, features, and characteristics of the present invention, as well as the methods of operation and functions of the related elements of the structure, and the combination of parts and economies of manufacture, will become more apparent upon consideration of the following detailed description with reference to the accompanying drawings, all of which form a part of this specification.

BRIEF DESCRIPTION OF THE DRAWINGS

A further understanding of the present invention can be obtained by reference to a preferred embodiment set forth in the illustrations of the accompanying drawings. Although the illustrated embodiment is merely exemplary of systems for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which.

DETAILED DESCRIPTION OF THE INVENTION

As required, a detailed illustrative embodiment of the present invention is disclosed herein. However, techniques, systems and operating structures in accordance with the present invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention. The following presents a detailed description of a preferred embodiment (as well as some alternative embodiments) of the present invention.

A length of stretchable woven material capable of longitudinal and transverse stretching is set flat wherein in its right sided longest half a suitable fastening means of nap pile patch is secured. A corresponding hook strip component is secured on the left adjacent half. A semi-cylindrical sponge like material with its flat surface up to the back of the nap pile fastening means is placed between the material and is enclosed by seams at its right and left side with permanent seams to the bottom length and the left side of the band. The band is then donned by placing the cylindrical surface over the sternum, extending and stretching the band to accommodate the circumference of the chest and in overlapping relationship secured with its fastener in the front of the chest onto the flat surface of the semi-cylindrical component. The band is of one piece construction which is easily applied to the patient while in bed from either right or left orientation.

Figure 1:
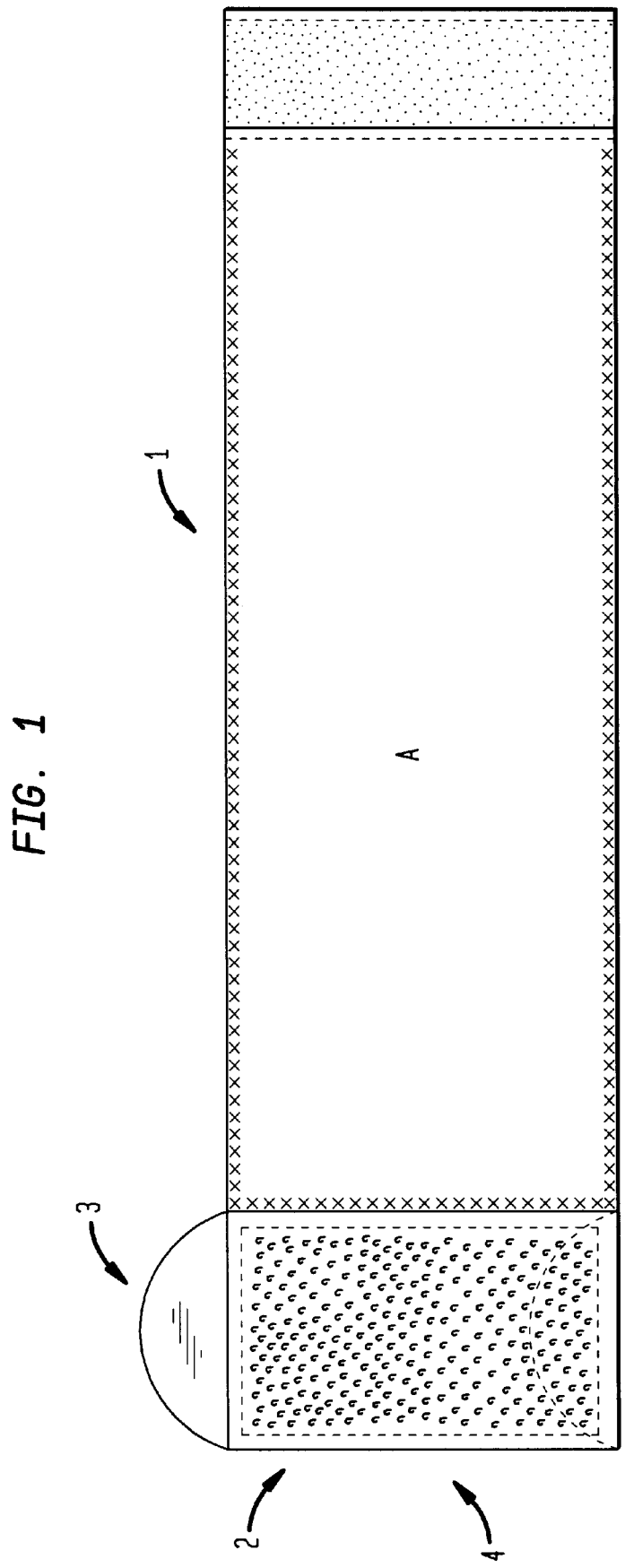
FIG. 1 is a perspective view of the solid band of the comfort band before it is applied to the patient.
Figure 2:
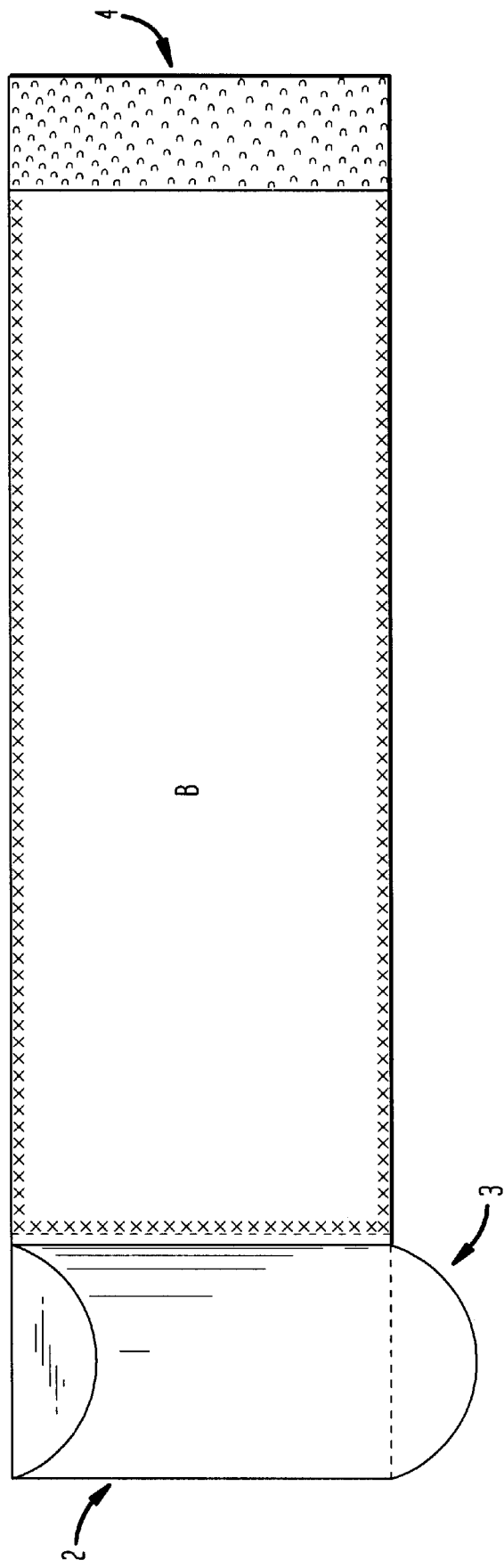
FIG. 2 is a perspective view of the solid band as it would be applied to the patient and the body engaging surface.
Figure 3:
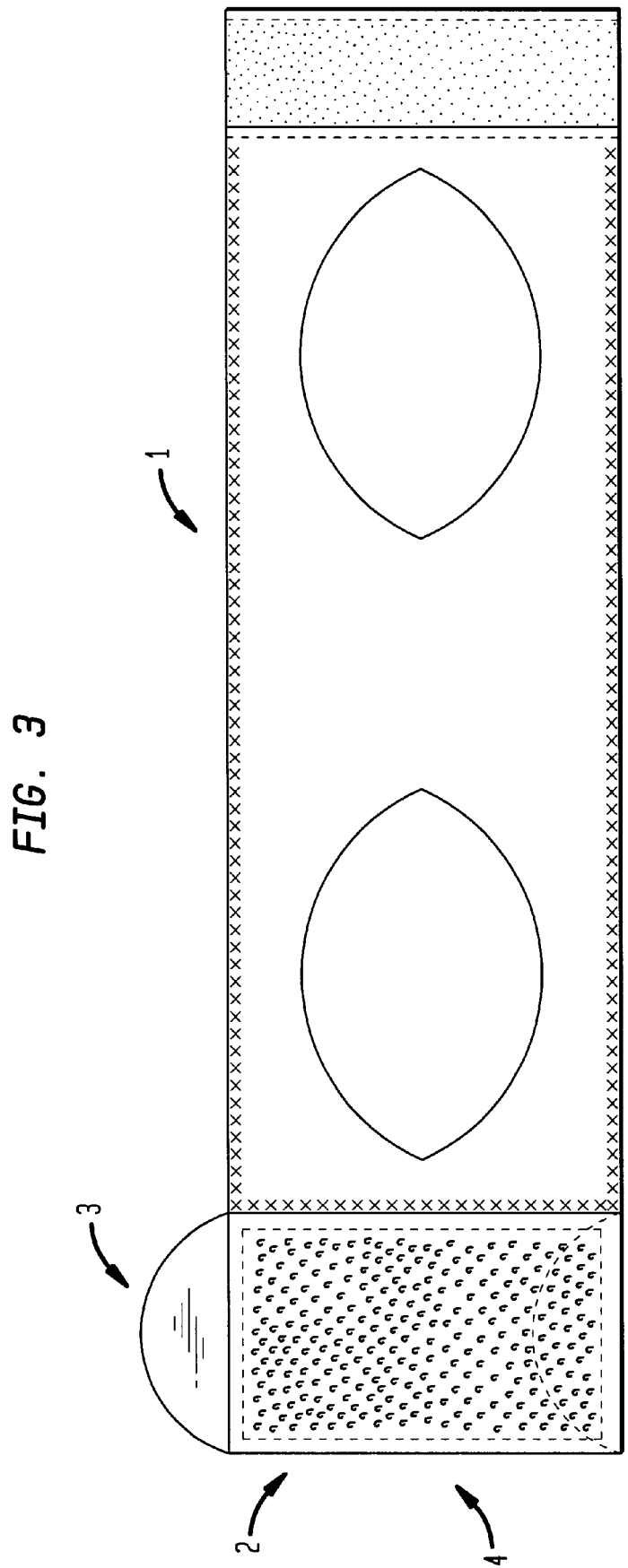
FIG. 3 is a perspective view of the Fenestrated band of the invention before it is applied to the patient.
Figure 4:
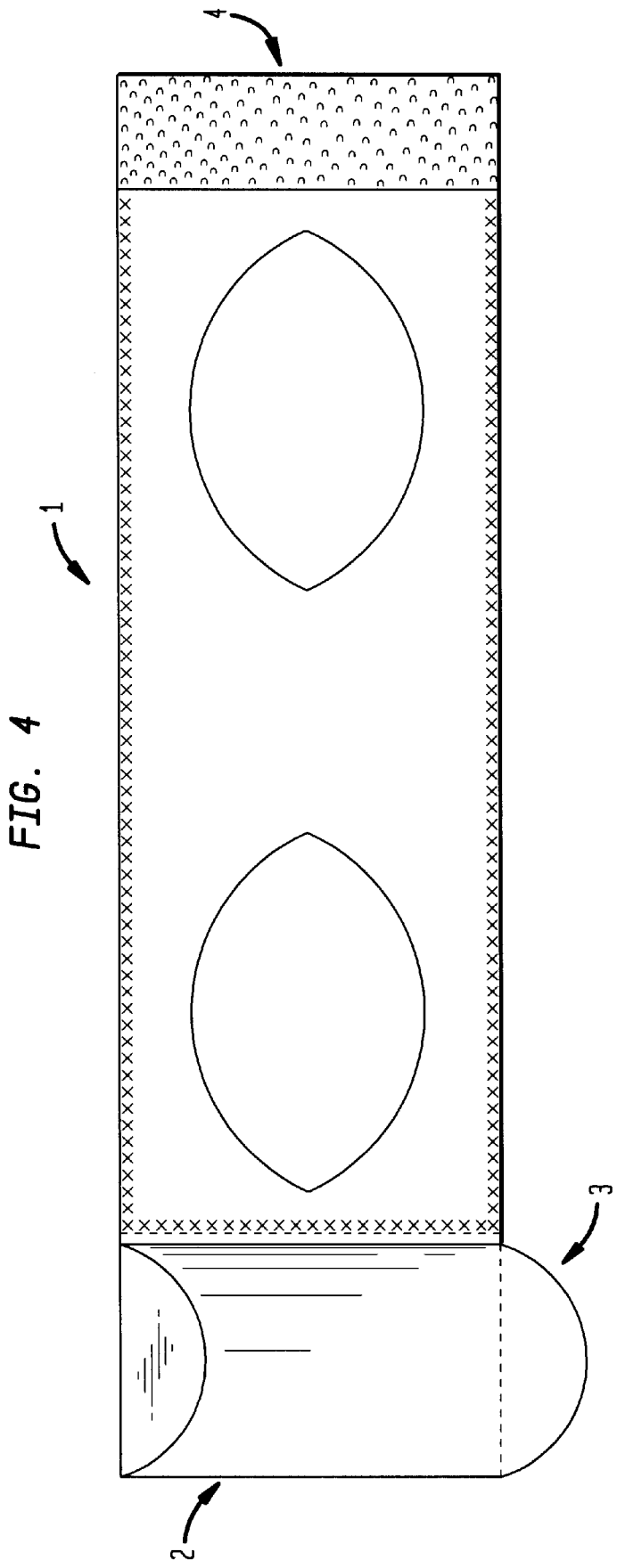
FIG. 4 is a perspective view of the Fenestrated band as it would be applied to the patient and the body engaging surface.

The stretchable and adaptable band or garment of the invention comprises of a relatively wide solid body band 1, FIGS. 1 & 2 which encircles the chest and accommodates breast coverage or breast exposure achieved with a Fenestrated band 1, FIGS. 3 & 4. The band end is connected to a space-occupying semi-cylindrical sponge-like material 2, FIGS. 1, 2, 3 & 4 which serves as a bolster for the breast.

In use, the cylindrical shaped surface at one end 3, FIGS. 1, 2, 3 & 4 is centrally placed over the sternum, the connecting band 1, FIGS. 1, 2, 3, & 4 is then wrapped under the arms around the chest and preferably secured in the front in overlapping relationship with a VELCRO™ (or similar hook and loop fastener) type fastener which provides for size adjustments.

The drawings depict the flat surface of the semi-cylindrical bolster as having a patch of material 4, FIGS. 1 & 3 comprising of multiple laterally spaced short strips of textile pile material wherein a plurality of hook strips 4, FIGS. 2 & 4 at the distal end and opposing side of the band is suitably attached to the outer pile material on the bolster when encircled around the body and fastened in the front.

As preferred, the strips of pile material is secured by secure and suitable stitching to the flat surface of the bolster which will receive the hook strips. Hook strips may be of a type such as is disclosed in U.S. Pat. No. 2,717,437, issued Sep. 13, 1955, wherein the hook strip is constructed with tiny fiber hook elements extending outwardly from one side of a backing material which will become embedded and adhere to the soft pile material when pressed against.

Because the fastening means is described and fully disclosed in said U.S. Pat. No. 2,717,437, a further description thereof is deemed unnecessary. In fact, it is to be understood that other fastening devices may be employed without departing from the invention. This also applies to the semi-cylindrical bolster which can be replaced by any other shape which accomplishes the means of support as a bolster and breast separator.

Referring now to FIG. 1, a stretchable and adaptable body conforming knit material of approximately 58 cm long by 20 cm wide of a material is laid out to its fullest dimensions which when folded in half lengthwise will yield a panel A, and panel B. With this orientation in mind, reopen it to its fullest dimensions.

Sew a permanent and secure patch of nap pile material of approximately 8 cm long by 5 cm wide with its length to the right edge of panel A, next maintaining original orientation sew a 8 cm by 5 cm patch of hook strips to the left edge of panel B. Fastening means have now been secured so that when the band is constructed and is encircled about the chest it will be in overlapping relationship to the pile material over the flat surface of panel A. Next flip panel A so that panel A now faces panel B and is inside out. Leaving a 5 mm free edge on top sew a permanent seam to the right edge of panels A and B together which will create a right angle pocket. By means of a scissor obtain a sponge-like material, cut and shape the semi-cylindrical bolster to the following dimension, flat wall surface 6.5 cm wide, height 9 cm, cylindrical depth dimension of 12.2 cm round from its flat wall surface so that it yields a total circumference of 18.7 cm. At its top and bottom base surfaces the above dimensions should yield a 4.8 cm wide flat surface from its 6.5 cm wall. Next, enclose and position the semi-cylindrical bolster to the extreme right between panel A and B with its flat surface facing panel A while the semi-cylindrical bolster faces panel B. Invert 5 mm of bottom edges of panel A and B and sew the length of the band leaving a 5 mm free edge to the left of the band. Sew a permanent and secure seam to the left of the semi-cylindrical bolster, securing it to its compartment.

Invert the free 5 mm left edges of panels A and B and sew permanent seams. The band is now fully constructed and ready to apply by placing the cylindrical surface of panel B over the sternum, between the breast and encircling the band around the back and chest so that the free end of the band with the hook strips may be fastened over the nap pile material of panel A.

Referring now to FIG. 2, a stretchable and adaptable body conforming knit material of approximately 60 cm long by 20 cm wide of a material is laid out to its fullest dimensions which when folded in half lengthwise will yield a panel A, and panel B. With this orientation in mind, reopen it to its fullest dimensions.

Sew a permanent and secure patch of nap pile material of approximately 8 cm long by 5 cm wide with its length to the right edge of panel A, next maintaining original orientation sew a 8 cm by 5 cm patch of hook strips to the left edge of panel B. Fastening means have now been secured so that when the band is constructed and is encircled about the chest it will be in overlapping relationship to the pile materials over the flat surface of panel A. Next flip panel A so that panel A now faces panel B and is inside out. Leaving a 5 mm free edge on top sew a permanent seam to the right edge of panels A and B together which will create a right angle pocket. By means of a scissor obtain a sponge-like material, cut and shape the semi-cylindrical bolster to the following dimension, flat wall surface 6.5 cm wide, height 9 cm, cylindrical depth dimension of 12.2 cm round from its flat wall surface so that it yields a total circumference of 18.7 cm. At its top and bottom base surfaces the above dimensions should yield a 4.8 cm wide flat surface from its 6.5 cm wall. Next, enclose and position the semi-cylindrical bolster to the extreme right between panel A and B with its flat surface facing panel A while the semi-cylindrical bolster faces panel B. Invert 5 mm of bottom edges of panel A and B and sew the length of the band leaving a 5 mm free edge to the left of the band. Sew a permanent and secure seam to the left border of the semi-cylindrical bolster, securing it to its compartment. Measure approximately 2 cm from this last seam, mark it. Next measure out and mark an ellipses measuring 11 cm long by 7 cm tall from 1.5 cm from the top and bottom edges so that its mid axis and highest point is at 90 degrees. Evenly cut fenestrations, invert its double edges approximately 2 mm's and seam edges of fenestration closed. From the left edge side of this fenestrations measure 24.5 cm on the band next measure out and cut the same dimensions of the first fenestration. Seam fenestrations edges closed together as before. Fenestrations are complete. Invert the free 5 mm left edges of panels A and B and sew together with permanent seams. The band is now fully constructed and ready to apply by placing the cylindrical surface of panel B over the sternum, between the breast and encircling the band around the back and chest so that the free end of the band with the hook strips may be fastened over the nap pile material of panel A.

While the present invention has been described with reference to one or more preferred embodiments, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention.

It should be appreciated that the present invention is capable of being embodied in other forms without departing from its essential characteristics.

What is claimed is:

1. A chest band for use for comfort and breast stabilization from lateral gravitational breast shifting while the user lays in the right or left lateral position comprising:

a stretchable and adaptable body strip disposed to encircle the body;

first and second sections of the length of said body strip;

wherein said first section further comprises a semi-cylindrical component of a sponge-like material at one end and a nap material patch on its outer surface with a cylindrical side placed over the sternum, between the breast;

and wherein said second section comprises a means for connecting an end of said body strip together in the form of a loop to encircle a user's body;

and wherein said chest band further comprises at least one fenestration to enable breast exposure.

2. A chest band according to claim 1 wherein said fenestrations are stretchable to accommodate breasts of various sizes.

* * * * *